(12) United States Patent
Wang et al.

(10) Patent No.: US 10,668,460 B2
(45) Date of Patent: Jun. 2, 2020

(54) COMPOSITE CATALYST, METHOD FOR MANUFACTURING COMPOSITE CATALYST AND APPLICATION THEREOF

(71) Applicants: ZHEJIANG NHU COMPANY LTD., Shaoxing (CN); ZHEJIANG UNIVERSITY, Hangzhou (CN); SHANDONG NHU PHARMACEUTICAL CO., LTD., Weifang (CN); SHANDONG NHU VITAMIN CO., LTD., Weifang (CN)

(72) Inventors: Yong Wang, Hangzhou (CN); Lili Yu, Shaoxing (CN); Xiao Ma, Weifang (CN); Jianyong Mao, Weifang (CN); Zhe Wang, Hangzhou (CN); Shanjun Mao, Hangzhou (CN); Jingsi Tang, Shaoxing (CN); Haoran Li, Hangzhou (CN); Zhirong Chen, Hangzhou (CN)

(73) Assignees: ZHEJIANG NHD COMPANY LTD., Shaoxing (CN); ZHEJIANG UNIVERSITY, Hangzhou (CN); SHANDONG NHU PHARMACEUTICAL CO., LTD., Weifang (CN); SHANDONG NHU VITAMIN CO., LTD., Weifang (CN)

( * ) Notice: Subject to any disclaimer, the term of this patent is extended or adjusted under 35 U.S.C. 154(b) by 0 days.

(21) Appl. No.: 16/669,524

(22) Filed: Oct. 31, 2019

(65) Prior Publication Data

US 2020/0070138 A1    Mar. 5, 2020

Related U.S. Application Data

(63) Continuation of application No. PCT/CN2019/071319, filed on Jan. 11, 2019.

(30) Foreign Application Priority Data

Aug. 31, 2018  (CN) .......................... 2018 1 1010567

(51) Int. Cl.
*B01J 37/02* (2006.01)
*B01J 37/04* (2006.01)
(Continued)

(52) U.S. Cl.
CPC ........... *B01J 37/0207* (2013.01); *B01J 23/42* (2013.01); *B01J 23/44* (2013.01); *B01J 23/462* (2013.01);
(Continued)

(58) Field of Classification Search
CPC .... B01J 37/0207; B01J 37/0209; B01J 37/04; B01J 37/06; B01J 37/16; B01J 21/18;
(Continued)

(56) References Cited

U.S. PATENT DOCUMENTS 8,709,964 B2 *  4/2014  Ewald ................... B01J 27/22
                                            429/523
8,962,513 B2 *  2/2015  Liu ....................... B01J 21/18
                                            502/177
(Continued)

FOREIGN PATENT DOCUMENTS

CN       105749948 A    7/2016
CN       106179440 A    12/2016
(Continued)

*Primary Examiner* — Patricia L. Hailey (57) ABSTRACT

A composite catalyst includes a carrier and noble metal particles supported by the carrier, wherein the carrier is a nitrogen-doped porous carbon composite material having a plurality of passages. The nitrogen-doped porous carbon composite material can include a nitrogen-doped porous carbon material and a plurality of metal oxide particles. The plurality of metal oxide particles can be uniformly distributed in the nitrogen-doped porous carbon material. The
(Continued)

plurality of metal oxide particles can be partially exposed through the plurality of passages. The noble metal particles can be tightly combined with the exposed metal oxide particles to achieve recombination. And the noble metal particles can be at least one of Pd metal particles, Pt metal particles, Ru metal particles, Rh metal particles, Ir metal particles, Au metal particles, or a combination thereof.

13 Claims, 5 Drawing Sheets

(51) Int. Cl.
    *B01J 35/10*     (2006.01)
    *C07D 495/04*     (2006.01)
    *C07C 5/05*     (2006.01)
    *B01J 37/16*     (2006.01)
    *B01J 23/42*     (2006.01)
    *B01J 23/44*     (2006.01)
    *B01J 23/46*     (2006.01)
    *B01J 37/08*     (2006.01)
    *B01J 21/18*     (2006.01)

(52) U.S. Cl.
    CPC ........... *B01J 23/464* (2013.01); *B01J 23/468* (2013.01); *B01J 35/10* (2013.01); *B01J 37/0209* (2013.01); *B01J 37/04* (2013.01); *B01J 37/08* (2013.01); *B01J 37/16* (2013.01); *C07C 5/05* (2013.01); *C07D 495/04* (2013.01); *B01J 21/18* (2013.01)

(58) Field of Classification Search
    CPC . B01J 23/42; B01J 23/44; B01J 23/462; B01J 23/464; B01J 23/468; B01J 35/10; C07C 5/05; C07D 495/04
    USPC .......................................... 502/182, 185, 200
    See application file for complete search history.

(56) References Cited

U.S. PATENT DOCUMENTS

| | | | |
|---|---|---|---|
| 2014/0107371 A1* | 4/2014 | Bakker | C07C 209/36 558/414 |
| 2015/0050583 A1* | 2/2015 | Schuth | B01J 37/084 429/524 |
| 2015/0343428 A1* | 12/2015 | Kim | B01J 35/026 502/185 |
| 2018/0078925 A1* | 3/2018 | Yoon | B01J 37/082 |

FOREIGN PATENT DOCUMENTS

| | | | | |
|---|---|---|---|---|
| CN | 106622327 A | | 5/2017 | |
| CN | 10 8660480 | * | 10/2018 | ............... C25B 1/04 |
| CN | 10 8927194 | * | 12/2018 | ............... B01J 27/24 |
| CN | 10 8940346 | * | 12/2018 | ............... B01J 27/24 |
| CN | 109277109 A | | 1/2019 | |
| CN | 10 9289886 | * | 2/2019 | ............... B01J 27/24 |
| CN | 10 9306499 | * | 2/2019 | ............... C25B 1/04 |
| CN | 106925267 A | | 7/2019 | |
| KR | 101473752 B1 | | 12/2014 | |

\* cited by examiner

COMPOSITE CATALYST, METHOD FOR MANUFACTURING COMPOSITE CATALYST AND APPLICATION THEREOF

CROSS-REFERENCE TO RELATED APPLICATIONS

This application is a continuation of PCT patent application PCT/CN2019/071319 filed on Jan. 11, 2019, which claims all benefits accruing under 35 U.S.C. § 119 from China Patent Application No. 201811010567.1, filed on Aug. 31, 2018, in the China National Intellectual Property Administration, the content of which is hereby incorporated by reference.

TECHNICAL FIELD

The present disclosure relates to the technical field of a catalyst, in particular, to a composite catalyst, method for manufacturing a composite catalyst and application thereof.

BACKGROUND

More than 80% of chemicals used in life are manufactured by specific catalytic processes. A key point of the catalytic process is the catalyst. Heterogeneous catalysts have received extensive attention due to their ease of operation. As an important representative of heterogeneous catalysts, supported metal nanocatalysts have been applied widely. Dispersing active metal particles on a carrier can greatly reduce the amount of metal consumption which can achieve the same catalytic effect. A carbon material has high thermal and electrical conductivity and chemical stability, and is an ideal catalyst carrier. However, noble metal nanoparticles are easily agglomerated due to the nano-scale and it is difficult to achieve high dispersion when noble metal nanoparticles are loaded by carbon materials.

SUMMARY

The present disclosure provides a composite catalyst, a method for manufacturing the composite catalyst and application thereof. The noble metal particles can be highly dispersed in the composite catalyst and thus the composite catalyst has an excellent catalytic property.

The present disclosure provides a composite catalyst including a carrier and noble metal particles supported by the carrier, wherein the carrier is a nitrogen-doped porous carbon composite material having a plurality of passages. The nitrogen-doped porous carbon composite material can include a nitrogen-doped porous carbon material and a plurality of metal oxide particles. The plurality of metal oxide particles can be uniformly distributed in the nitrogen-doped porous carbon material. The plurality of metal oxide particles can be partially exposed through the plurality of passages. Noble metal atoms of the noble metal particles can be tightly combined with oxide atoms of the exposed metal oxide particles to achieve recombination. And the noble metal particles can be at least one of Pd metal particles, Pt metal particles, Ru metal particles, Rh metal particles, Ir metal particles, Au metal particles, or a combination thereof.

The noble metal particles can have a dispersity of 75% to 95% in the nitrogen-doped porous carbon composite material.

A weight percentage of the noble metal particles in the composite catalyst can be in a range of 0.1% to 10%. A weight percentage of the metal oxide particles in the composite catalyst can be in a range of 2% to 30%. A weight percentage of the nitrogen-doped porous carbon composite material in the composite catalyst can be in a range of 60% to 97.9%. And a weight percentage of nitrogen element in the nitrogen-doped porous carbon composite material can be in a range of 0.5% to 15%.

A method for manufacturing a composite catalyst can include the following steps:
dissolving a metal source in a solvent to obtain a premix;
sequentially adding a nitrogen-containing biomass and a pore-forming agent to the premix, such that the metal source reacts with the pore-forming agent to obtain a mixture containing a metal precipitate, wherein the pore-forming agent can be at least one of ammonium bicarbonate, ammonium carbonate, ammonium oxalate, ammonium hydrogen oxalate, oxalic acid, or a combination thereof, and a molar ratio of the metal source to the pore-forming agent is in a range of 1:1 to 1:20;
treating the mixture by a first calcination at 500 degrees centigrade to 1200 degrees centigrade under an inert atmosphere to obtain a nitrogen-doped porous carbon composite material having a plurality of passages, wherein the nitrogen-doped porous carbon composite material can include a nitrogen-doped porous carbon material and a plurality of metal oxide particles, the plurality of metal oxide particles can be uniformly distributed in the nitrogen-doped porous carbon material, and a part of the plurality of metal oxide particles can be exposed through the plurality of passages; and
forming noble metal particles in the plurality of passages and combining noble metal atoms with oxide atoms of the exposed part of the plurality of metal oxide particles.

The step of forming noble metal particles in the plurality of passages can be as following:
immersing the nitrogen-doped porous carbon composite material in a noble metal precursor solution; and
treating the nitrogen-doped porous carbon composite material by a second calcination and a hydrogen reduction to obtain noble metal particles in the plurality of passages.

The step of forming noble metal particles in the plurality of passages can be as following:
immersing the nitrogen-doped porous carbon composite material in a noble metal precursor solution; and
adding a reductant which reacts with a noble metal precursor of the noble metal precursor solution to obtain noble metal particles in the plurality of passages.

A noble metal precursor in the noble metal precursor solution can be at least one of $PdCl_2$, $H_2PdCl_4$, $Pd(NO_3)_2$, $Pd(NH_3)_4(NO_3)_2$, $H_2PtCl_6 \cdot 6H_2O$, $[Pt(NH_3)_4](NO_3)_2$, $Na_2PtCl_4 \cdot xH_2O$, $H_8C_{14}N_2Pt$, $PtCl_4$, $Pt(C_5H_7O_2)_2$, $C_{10}H_{14}O_4Pt$, $(NH_4)_2RuCl_6$, $RuCl_3$, $C_{15}H_{21}O_6Ru$, $H_{12}C_{16}N_3Rh$, $RhN_3O_9$, $RhCl_3 \cdot 3H_2O$, $IrCl_3$, $Na_2IrCl_6 \cdot 6H_2O$, $H_2IrCl_6 \cdot xH_2O$, $[CH_3COCH\!=\!C(O\!-\!)CH_3]_3Ir$, $NaAuCl_4 \cdot 2H_2O$, $HAuCl_4 \cdot XH_2O$, $(NH_4)AuCl_4$, or a combination thereof.

In the second calcination, a calcination temperature can be in a range of 200 degrees centigrade to 500 degrees centigrade, a heating rate can be in a range of 1 degree centigrade per minute to 20 degrees centigrade per minute, and the time can be in a range of 1 minute to 240 minutes. In the hydrogen reduction, a reduction temperature can be in a range of 150 degrees centigrade to 500 degrees centigrade, a heating rate can be in a range of 1 degree centigrade per minute to 20 degrees centigrade per minute, the time can be in a range of 1 minute to 360 minutes, and a flow rate of hydrogen gas can be in a range of 20 milliliters per minute to 200 milliliters per minute.

The reductant can be at least one of NaBH₄, HCOOH, hydrazine hydrate, or a combination thereof, and a molar ratio of the reductant to the noble metal precursor of the noble metal precursor solution is in a range of 1:1 to 1000:1.

The metal source can be at least one of cerium nitrate, zirconium nitrate, aluminum nitrate, or a combination thereof, the solvent is water, and the nitrogen-containing biomass can be at least one of bamboo, chitin, carboxymethyl chitin, chitosan, carboxymethyl chitosan, glucosamine hydrochloride, or a combination thereof.

A mass ratio of the metal source to the nitrogen-containing biomass can be in a range of 0.05:1 to 2:1.

A calcination time during the first calcination can be in a range of 0.1 hour to 5 hours.

The Composite catalyst and the method for manufacturing the same have the following advantages.

The pore-forming agent can play a role as below: on the one hand, a carbonate ion or a hydrogen carbonate ion in the pore-forming agent can react with an metal ion in the metal source to obtain the metal precipitate uniformly distributed; on the other hand, the pore-forming agent and metal precipitate can be decomposed during the subsequent calcination, and a gas can be generated, forming the plurality of passages in the nitrogen-doped porous carbon material. During the process of calcination, the metal precipitate can be decomposed to form nanoscale metal oxide particles. Finally, the metal oxide particles can be uniformly distributed in the nitrogen-doped porous carbon material, and a part of the surface of the metal oxide particles can be exposed through the plurality of passages. It should be noted that in the reaction of the pore-forming agent and the metal source, the pore-forming agent does not need to be excessive relative to the metal source, and even if the carbonate or oxalate in the pore-forming agent is transferred into the metal precipitate, the metal precipitate can be also decomposed and the gas can be generated in order to form a pore-forming effect.

In a heat treatment of the first calcination, it can achieve a strong interaction bond between the noble metal particles and the exposed metal oxide particles. Moreover, by utilizing the oxygen vacancies of the metal oxide, noble metal atoms can be also combined with atoms in metal oxide to achieve a recombination and being firmly supported on the carrier. That is, since the metal oxide particles can be dispersed in the nitrogen-doped porous carbon composite material, the noble metal particles can be also highly dispersed in the nitrogen-doped porous carbon composite material, avoiding noble metal particles aggregated during the reduction process. The manufacturing method is simple. The noble metal particles can be highly dispersed by the metal oxide, so the loading efficiency of the noble metal particles can be high. The noble metal in the obtained composite catalyst can have a large specific surface area which is also beneficial for adsorption of a reactant and the composite catalyst has high catalytic activity.

The present disclosure also provides an application of a composite catalyst as a catalyst in a selective hydrogenation reaction of an unsaturated ketone or a biotin precursor, and a structure of the biotin precursor is as below:

The unsaturated ketone can be at least one of 6-methyl-5-hepten-2-one, 6,10-dimethyl-5-undecen-2-one, 6,10-dimethyl-5,9-undecenediene-2-one, 6,10,14-trimethyl-5-pentadecen-2-one, 6,10,14-trimethyl-5,9-pentadecandien-2-one, 6,10,14-trimethyl-5,9,13-pentadecatrien-2-one, or a combination thereof.

Since the structure of the noble metal particles in the composite catalyst is stable, the composite catalyst can be reused multiple times.

DETAILED DESCRIPTION

The technical solutions of the embodiments of the present disclosure are clearly and completely described below. It is obvious that the described embodiments are only a part and not all of the embodiments of the present disclosure. All other embodiments obtained by one skilled in the art based on the embodiments of the present disclosure without any creative efforts are within the scope of the present disclosure.

The present disclosure provides a method for manufacturing a composite catalyst. The method includes the following steps:

S1, dissolving a metal source in a solvent to obtain a premix;

S2, sequentially adding a nitrogen-containing biomass and a pore-forming agent to the premix, such that the metal source reacts with the pore-forming agent to obtain a mixture containing a metal precipitate, wherein the pore-forming agent is at least one of ammonium bicarbonate, ammonium carbonate, ammonium oxalate, ammonium hydrogen oxalate, oxalic acid, or a combination thereof, and a molar ratio of the metal source to the pore-forming agent is in a range of 1:1 to 1:20;

S3, treating the mixture by a first calcination at 500 degrees centigrade to 1200 degrees centigrade under an inert atmosphere to obtain a nitrogen-doped porous carbon composite material having a plurality of passages, wherein the nitrogen-doped porous carbon composite material comprises a nitrogen-doped porous carbon material and a plurality of metal oxide particles, the plurality of metal oxide particles are uniformly distributed in the nitrogen-doped porous carbon material, and a part of the plurality of metal oxide particles are exposed through the plurality of passages; and S4, forming noble metal particles in the plurality of passages and combining noble metal atoms with oxide atoms of the exposed part of the plurality of metal oxide particles.

In the step S1, the metal source can play a role of carrying a noble metal catalyst. The metal source needs to be soluble in the solvent. In one embodiment, the metal source can be at least one of cerium nitrate, zirconium nitrate, aluminum nitrate, or a combination thereof, and the solvent can be water. A ratio of the metal source to the solvent is not limited. In one embodiment, a ratio of a mass of the metal source to a volume of the solvent can be 1 g:100 mL to 10 g:100 mL.

The nitrogen-containing biomass can be at least one of bamboo, chitin, carboxymethyl chitin, chitosan, carboxymethyl chitosan, glucosamine hydrochloride, or a combination thereof. The nitrogen-containing biomass can include a nitrogen element and a carbon element as a nitrogen source and a carbon source, respectively. The nitrogen-containing biomass can be insoluble in the water.

The metal source can react with a part of the pore-forming agent to form the metal precipitate. The metal precipitate can be formed by carbonate ions and metal ions. An excess part of the pore-forming agent can decompose during subsequent calcination to form a gas which plays a role of forming pore and results in the plurality of passages in the nitrogen-doped porous carbon material. In one embodiment, the mass ratio of the metal oxide to the nitrogen-containing biomass can be 0.05:1 to 2:1. In another embodiment, the mass ratio of the metal oxide to the nitrogen-containing biomass can be 0.5:1 to 2:1. There can be a continuous stirring for 0.1 hour to 10 hours during the reaction. The obtained mixture is actually a suspension, in which the metal precipitate formed and the nitrogen-containing biomass are insoluble in a solvent, but are evenly distributed in the mixture. So, the mixture is a suspension.

It will be understood that the mixture can be dried before the first calcination step of S3, and a process of drying can be as following: drying at a temperature with a range of 60 degrees centigrade to 180 degrees centigrade.

In step S3, the time of the first calcination can be in a range of 0.1 hour to 5 hours. In one embodiment, a process of the first calcination can be as follows: the temperature is raised to a range of 500 degrees centigrade to 1200 degrees centigrade at a heating rate of 2 degrees centigrade per minute to 30 degrees centigrade per minute, the mixture is calcined at the temperature of 500 degrees centigrade to 1200 degrees centigrade for 0.1 hour to 5 hours and finally naturally cooled to a room temperature. In another embodiment, the temperature of the first calcination can be from 600 degrees centigrade to 900 degrees centigrade.

In step S4, the noble metal particles can be at least one of Pd metal particles, Pt metal particles, Ru metal particles, Rh metal particles, Ir metal particles, Au metal particles, or a combination thereof. A loading amount (i.e., mass fraction) of the noble metal particles in the composite catalyst can be regulated, which is not limited. There can be two methods for forming the noble metal particles in the plurality of passages of the nitrogen-doped porous carbon composite material: one is a dipping method, and the other is a liquid phase reduction method.

The dipping method can be as follows: immersing the nitrogen-doped porous carbon composite material in the noble metal precursor solution; and subsequently treating the nitrogen-doped porous carbon composite material by the second calcination and hydrogen reduction in order. Noble metal particles can be formed in the plurality of passages of the nitrogen-doped porous carbon composite. In the second calcination of one embodiment, the temperature can be in a range of 200 degrees centigrade to 500 degrees centigrade, the heating rate can be in a range of 1 degree centigrade per minute to 20 degrees centigrade per minute, and the time is in a range of 1 minute to 240 minutes. In the hydrogen reduction, the temperature is in a range of 150 degrees centigrade to 500 degrees centigrade, the heating rate is in a range of 1 degree centigrade per minute to 20 degrees centigrade per minute, the time is in a range of 1 minute to 360 minutes, and a flow rate of hydrogen gas is in a range of 20 milliliters per minute to 200 milliliters per minute. In another embodiment, in the second calcination, the temperature can be in a range of 300 degrees centigrade to 500 degrees centigrade, the heating rate can be in a range of 5 degrees centigrade per minute to 10 degrees centigrade per minute, and the time can be in a range of 60 minutes to 120 minutes; in the hydrogen reduction, the temperature can be in a range of 200 degrees centigrade to 400 degree centigrade, the heating rate can be in a range of 5 degrees centigrade per minute to 10 degrees centigrade per minute, the time can be in a range of 60 minutes to 180 minutes, and the flow rate of hydrogen gas can be in a range of 40 milliliters per minute to 100 milliliters per minute.

The liquid phase reduction method can be as follows: immersing the nitrogen-doped porous carbon composite material in a noble metal precursor solution; and adding a reductant which reacts with a noble metal precursor of the noble metal precursor solution to obtain noble metal particles in the plurality of passages.

The noble metal precursor in the Noble metal precursor solution can be at least one of $PdCl_2$, $H_2PdCl_4$, $Pd(NO_3)_2$, $Pd(NH_3)_4(NO_3)_2$, $H_2PtCl_6 \cdot 6H_2O$, $[Pt(NH_3)_4](NO_3)_2$, $Na_2PtCl_4 \cdot xH_2O$, $H_8C_{14}N_2Pt$, $PtCl_4$, $Pt(C_5H_7O_2)_2$, $C_{10}H_{14}O_4Pt$, $(NH_4)_2RuCl_6$, $RuCl_3$, $C_{15}H_{21}O_6Ru$, $H_{12}Cl_6N_3Rh$, $RhN_3O_9$, $RhCl_3 \cdot 3H_2O$, $IrCl_3$, $Na_2IrCl_6 \cdot 6H_2O$, $H_2IrCl_6 \cdot xH_2O$, $[CH_3COCH{=}C(O{-})CH_3]_3Ir$, $NaAuCl_4 \cdot 2H_2O$, $HAuCl_4 \cdot XH_2O$, or $(NH_4)AuCl_4$, or a combination thereof.

The reductant can be at least one of $NaBH_4$, HCOOH, hydrazine hydrate, or a combination thereof. And a molar ratio of the reductant to the noble metal precursor of the noble metal precursor solution can be in a range of 1:1 to 1000:1.

The present disclosure further provides a composite catalyst including a carrier and noble metal particles supported by the carrier. The carrier can be a nitrogen-doped porous carbon composite material having a plurality of passages. Noble metal particles can be distributed in the plurality of passages. The nitrogen-doped porous carbon composite material can include a nitrogen-doped porous carbon material a plurality of metal oxide particles. The plurality of metal oxide particles can be uniformly distributed in the nitrogen-doped porous carbon material. The plurality of metal oxide particles can be partially exposed through the plurality of passages. Noble metal atoms can be tightly combined with oxide atoms of the exposed metal oxide particles to achieve recombination. The noble metal particles are at least one of Pd metal particles, Pt metal particles, Ru metal particles, Rh metal particles, Ir metal particles, Au metal particles. The noble metal particles can have a dispersity of 75% to 95% in the nitrogen-doped porous carbon composite material.

A weight percentage of the noble metal particles in the composite catalyst can be in a range of 0.1% to 10%. A weight percentage of the plurality of the metal oxide in the composite catalyst can be in a range of 2% to 30%. A weight percentage of the nitrogen-doped porous carbon composite material in the composite catalyst can be in a range of 60% to 97.9%. And a weight percentage of nitrogen element in the nitrogen-doped porous carbon composite material can be in a range of 0.5% to 15%.

Figure 5:
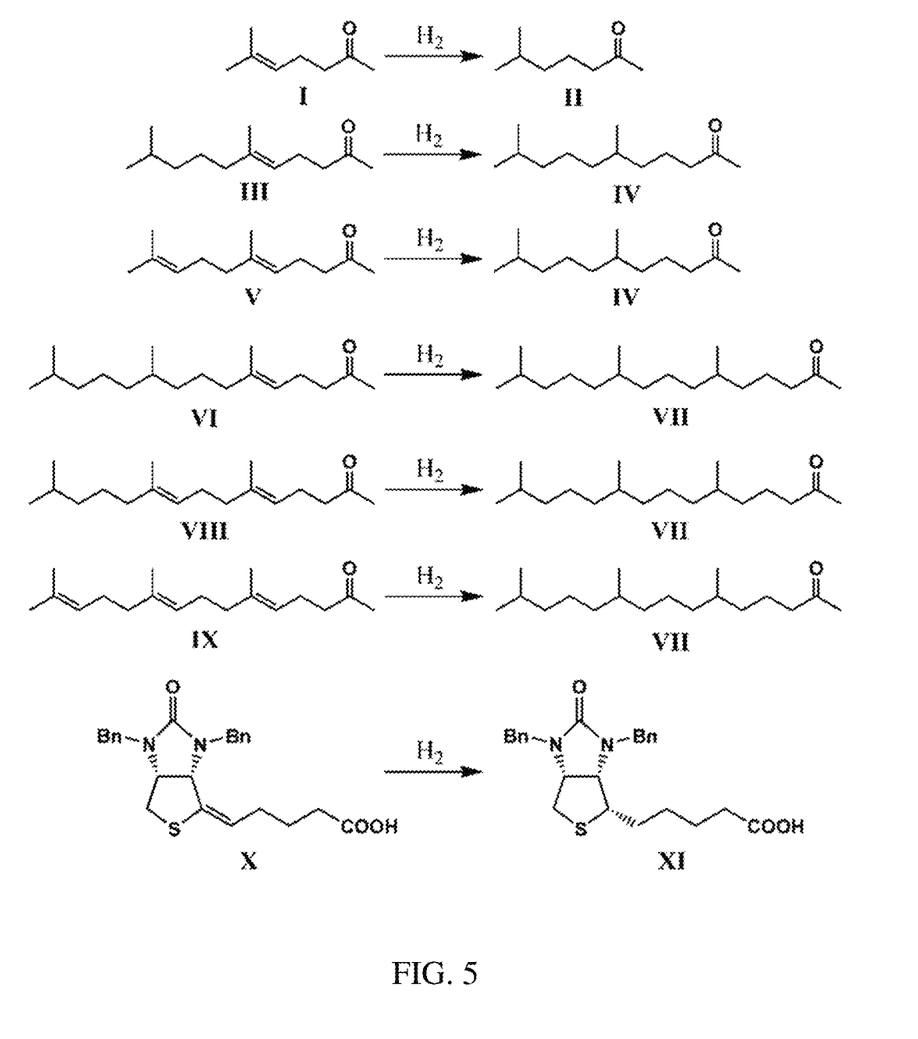
FIG. 5 is a schematic view showing processes of selective hydrogenations using composite catalysts in the present disclosure.

Referring to FIG. 5, the present disclosure also provides an application of the composite catalyst in a catalytic hydrogenation reaction. The composite catalyst can act as a catalyst in a selective hydrogenation reaction of an unsaturated ketone or a biotin precursor (X). And the unsaturated ketone is at least one of 6-methyl-5-hepten-2-one (I), 6,10-dimethyl-5-undecen-2-one (III), 6,10-dimethyl-5,9-undecenediene-2-one (V), 6,10,14-trimethyl-5-pentadecen-2-one (VI), 6,10,14-trimethyl-5,9-pentadecandien-2-one (VIII), 6,10,14-trimethyl-5,9,13-pentadecatrien-2-one (IX), or a combination thereof.

The composite catalyst of the present disclosure and its application will be further described below by multiple embodiments.

Embodiment 1

Approximately 1 g cerium nitrate hexahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 40 mL deionized water. Approximately 0.5 mL $PdCl_2$ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained. A theoretical loading amount (weight percentage) of Pd metal particles in the composite catalyst was 0.6%.

An actual loading amount of Pd metal particles in the composite catalyst was about 0.59% measured by atomic emission spectroscopy, which was approximately consistent with the theoretical load amount of Pd metal particles in the composite catalyst.

Figure 1:
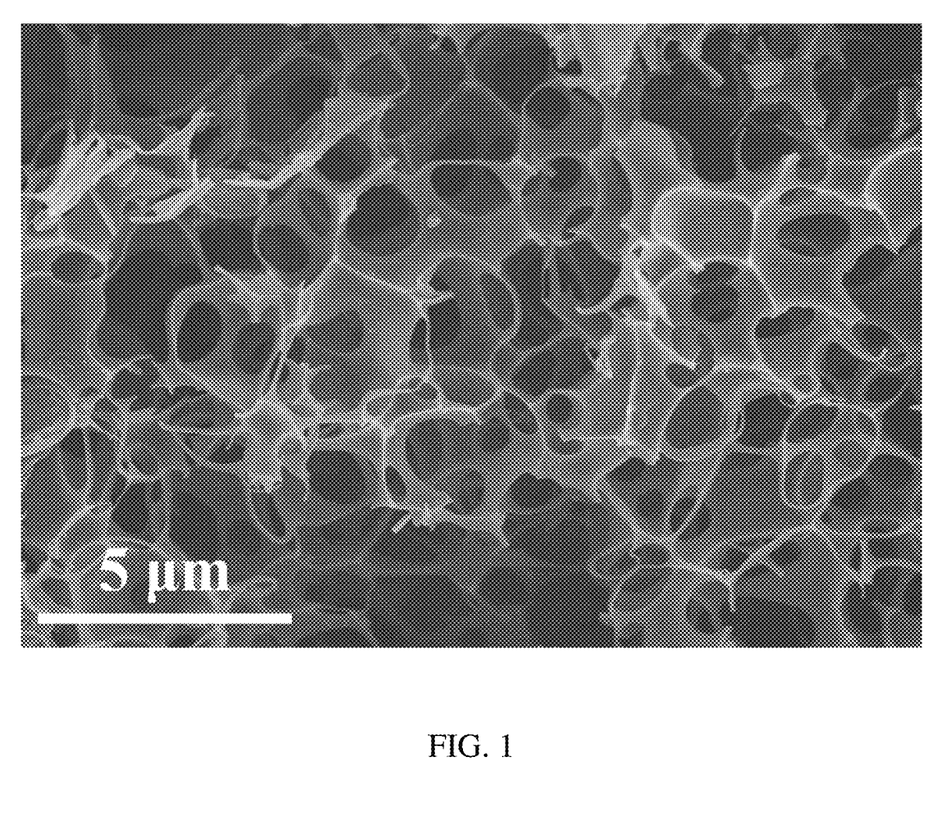
FIG. 1 is a scanning electron micrograph of a nitrogen-doped porous carbon composite material in embodiment 1.

The nitrogen-doped porous carbon composite material was measured by a scanning electron microscopy, and the result was shown in FIG. 1. Referring to FIG. 1, a plurality of pores and passages can be clearly observed.

Figure 2:
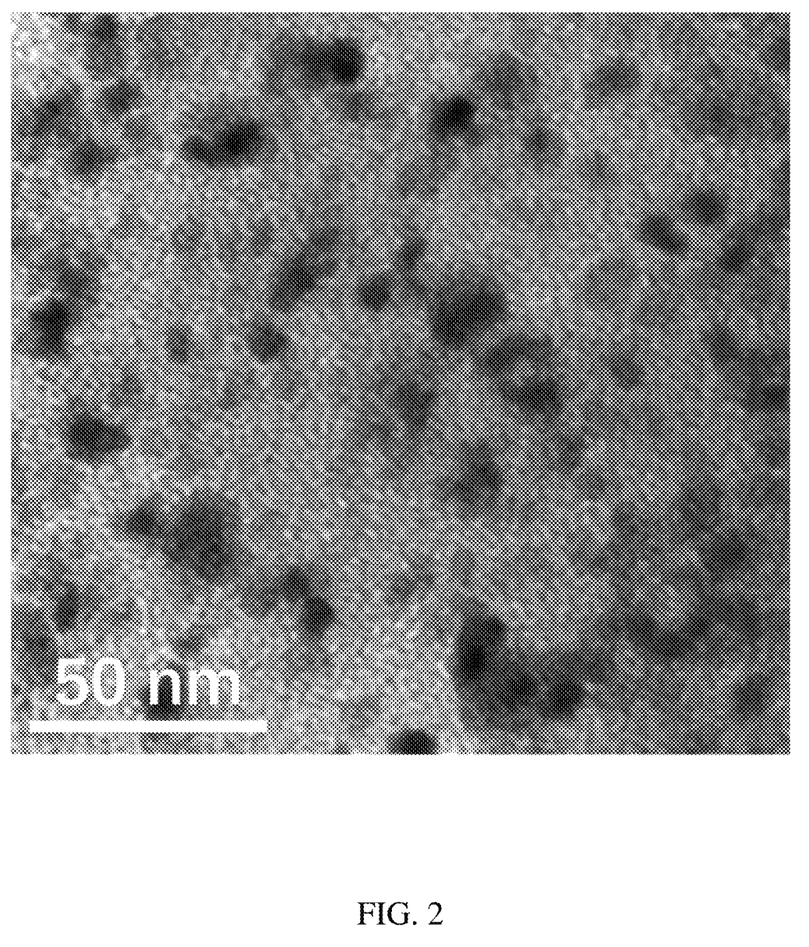
FIG. 2 is a transmission electron micrograph of a nitrogen-doped porous carbon composite material in embodiment 1.
Figure 3:
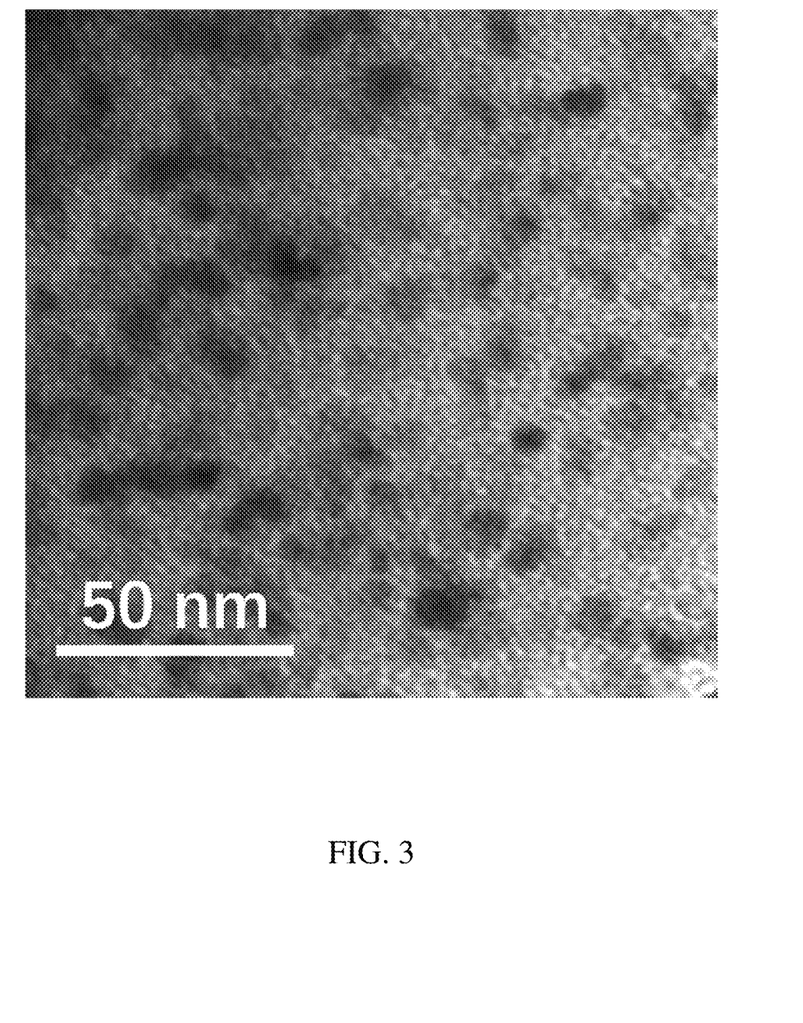
FIG. 3 is a transmission electron micrograph of a composite catalyst in embodiment 1.

The nitrogen-doped porous carbon composite was measured by a transmission electron microscopy, and the result was shown in FIG. 2. The composite catalyst was measured by a transmission electron microscopy, and the result was shown in FIG. 3. Comparing FIG. 2, the morphology of composite catalyst in FIG. 3 is substantially unchanged. It is difficult to see Pd metal particles in FIG. 3 because the size of Pd metal particles is very small and below 1 nm.

Figure 4:
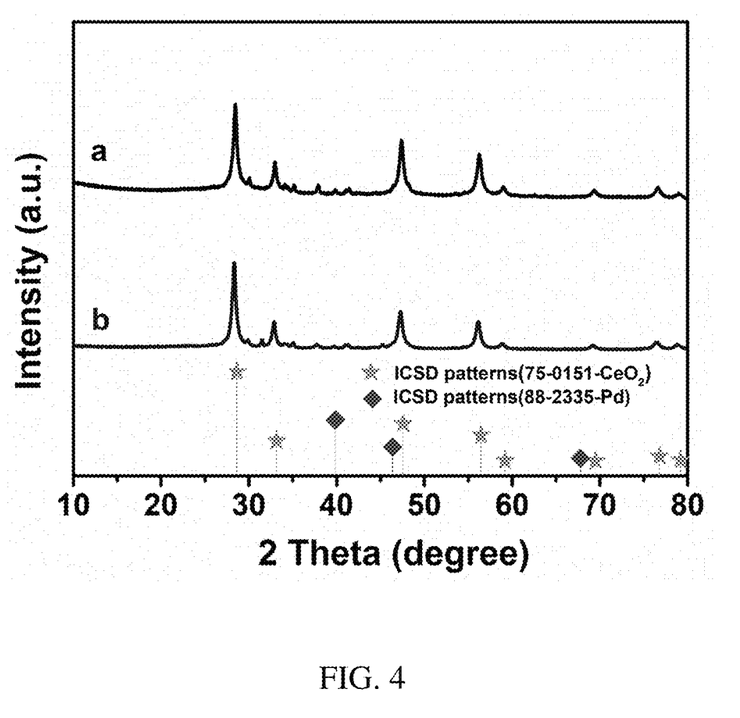
FIG. 4 is an X-ray photoelectron spectroscopy of a nitrogen-doped porous carbon composite material and a composite catalyst in embodiment 1, wherein a is corresponding to the nitrogen-doped porous carbon composite material, and b is corresponding to the composite catalyst.

The nitrogen-doped porous carbon composite and composite catalyst were measured by a X-ray photoelectron spectroscopy, and the result were shown in FIG. 4. Referring to FIG. 4, the curve a corresponding to nitrogen-doped porous carbon composite had no Pd diffraction characteristic peak. Compared with the standard card of Pd, the curve b corresponding to the compound catalyst was not obvious, which also confirmed the conclusion that Pd metal particles obtained in FIG. 3 were below 1 nm.

Pd dispersion and specific surface area of the composite catalyst were measured by CO titration method, wherein CO titration method is a carbon monoxide adsorption test for measuring noble metal dispersion. The results were: the Pd dispersion of the composite catalyst was about 83%, and the specific surface area of the composite catalyst was about 135.3 $m^2$ $g^{-1}$.

For comparison, a comparative embodiment 1 was also provided. The method of the composite catalyst in the comparative embodiment 1 was substantially the same as that of the composite catalyst in embodiment 1, except that there was no carboxymethyl chitin, only Pd was supported by $CeO_2$ to obtain a $Pd/CeO_2$ catalyst having a specific surface area of only 5.6 $m^2$ $g^{-1}$.

Embodiment 2

Approximately 1 g cerium nitrate hexahydrate was weighed and dispersed in about 30 mL water. After the indium nitrate hydrate was dissolved, about 3 g chitosan was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to about 40 mL deionized water. About 0.5 mL $PdCl_2$ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), composite catalyst was obtained.

The method of the composite catalyst in embodiment 2 was substantially the same as that of the composite catalyst in embodiment 1, except that the nitrogen-containing biomass was the chitosan.

Pd dispersion and specific surface area of the composite catalyst were measured by CO titration method. The results were: the Pd dispersion of the composite catalyst was about 81%, and the specific surface area of the composite catalyst was about 147.3 m² g⁻¹.

Embodiment 3

Approximately 1 g zirconium nitrate pentahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 40 mL deionized water. Approximately 0.5 mL PdCl₂ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained.

Pd dispersion and specific surface area of the composite catalyst were measured by CO titration method. The results were: the Pd dispersion of the composite catalyst was about 79%, and the specific surface area of the composite catalyst was about 126.8 m² g⁻¹.

Embodiment 4

Approximately 1 g aluminum nitrate nonahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 40 mL deionized water. Approximately 0.5 mL PdCl₂ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained.

Pd dispersion and specific surface area of the composite catalyst were measured by CO titration method. The results were: the Pd dispersion of the composite catalyst was about 76%, and the specific surface area of the composite catalyst was about 115.5 m² g⁻¹.

Embodiment 5

Approximately 1 g cerium nitrate hexahydrate was weighed and dispersed in approximately 30 mL water. After the cerium nitrate hexahydrate was dissolved, approximately 3 g chitosan was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 60 mL deionized water. Approximately 0.5 mL PdCl₂ solution with a molar concentration of about 10 mg/mL was slowly added dropwise and sonicated at about 25 degrees centigrade for about 30 minutes. Approximately 10.7 mL NaBH₄ solution with a molar concentration of about 2 mg/mL was then slowly added and continued to sonicate for about 30 minutes. After filtered, washed with deionized water to neutral and placed in an oven of about 70 degrees centigrade for about 24 h, a composite catalyst was obtained.

Pd dispersion and specific surface area of the composite catalyst were measured by CO titration method. The results were: the Pd dispersion of the composite catalyst was about 89%, and the specific surface area of the composite catalyst was about 138.7 m² g⁻¹.

Embodiment 6

Approximately 1 g cerium nitrate hexahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 40 mL deionized water. Approximately 0.8 mL H₂PtCl₆·6H₂O solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained.

Pt dispersion and specific surface area of the composite catalyst were measured by CO titration method. The results were: the Pt dispersion of the composite catalyst was about 91%, and the specific surface area of the composite catalyst was about 133.5 $m^2\ g^{-1}$.

Embodiment 7

Approximately 1 g cerium nitrate hexahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 60 mL deionized water. Approximately 0.7 mL $RuCl_3$ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained.

Ru dispersion and specific surface area of the composite catalyst were measured by CO titration method. The results were: the Ru dispersion of the composite catalyst was about 82%, and the specific surface area of the composite catalyst was about 133.9 $m^2\ g^{-1}$.

Embodiment 8

Approximately 1 g cerium nitrate hexahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 60 mL deionized water. Approximately 1.1 mL $H_{12}Cl_6N_3Rh$ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained.

Rh dispersion and specific surface area of the composite catalyst were measured by CO titration method. The results were: the Rh dispersion of the composite catalyst was about 83%, and the specific surface area of the composite catalyst was about 139.2 $m^2\ g^{-1}$.

Embodiment 9

Approximately 1 g cerium nitrate hexahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 60 mL deionized water. Approximately 0.9 mL $H_2IrCl_6 \cdot xH_2O$ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained.

Ir dispersion and specific surface area of the composite catalyst were measured by CO titration method. The results were: the Ir dispersion of the composite catalyst was about 81%, and the specific surface area of the composite catalyst was about 128.4 $m^2\ g^{-1}$.

Embodiment 10

Approximately 1 g cerium nitrate hexahydrate was weighed and dispersed in approximately 30 mL water. After the cerium nitrate hexahydrate was dissolved, approximately 3 g carboxymethyl chitin was added and stirred for about 1 hour. Then approximately 3 g ammonium bicarbonate was slowly added and stirred for about 1 hour to obtain a mixture. Then the temperature rose to about 80 degrees centigrade while stirring until dry. Then, the mixture was transferred to a crucible and underwent a calcination process in a nitrogen furnace. The calcination process was as follows: heating to about 1000 degrees centigrade at a heating rate of about 5 degrees centigrade per minute, calcining at about 1000 degrees centigrade for about 1 hour; then, naturally cooling to room temperature. The mixture calcined was ground to obtain a nitrogen-doped porous carbon composite.

Approximately 0.5 g nitrogen-doped porous carbon composite material was weighed and added to approximately 60 mL deionized water. Approximately 0.6 mL $HAuCl_4 \cdot XH_2O$ solution with a molar concentration of about 10 mg/mL was slowly added dropwise, stirred at about 50 degrees centigrade for about 12 h, and placed in an oven of about 70 degrees centigrade for about 24 h. It was further calcined at about 300 degrees centigrade for about 1 h in the air. Finally, after a hydrogen reduction at about 300 degrees centigrade for about 1 h (wherein, a flow rate of hydrogen gas was about 50 milliliters per minute, heating rate was about 5 degrees centigrade per minute), a composite catalyst was obtained.

Au dispersion and specific surface area of the composite catalyst were measured by CO titration method. The results were: Au dispersion of the composite catalyst was about 88%, and the specific surface area of the composite catalyst was about 137.3 $m^2 \, g^{-1}$.

Referring to FIG. 5, the processes of the hydrogenation reaction in the following embodiments were showed.

Embodiment 11

The composite catalyst catalyzes a selective hydrogenation of 6-methyl-5-hepten-2-one (I) by following process.

Approximately 50 mg composite catalyst obtained in embodiment 1 was added to a 50 mL autoclave. Approximately 15 mmol 6-methyl-5-hepten-2-one (I) and about 5 mL ethanol were added. The reaction was taken under a hydrogen pressure of about 2 MPa, a reaction temperature of about 30 degrees centigrade and reaction time of about 4 hours. A conversion of 6-methyl-5-hepten-2-one (I) was about 100%, and a selectivity of 6-methyl-2-heptanone (II) was about 99%. Further, a conversion and selectivity of the $Pd/CeO_2$ catalyst of the comparative embodiment 1 were about 68% and about 99%, respectively. Thus, the highly dispersed composite catalyst in embodiment 1 has greatly improved the selectivity of the catalyst while maintaining the activity of the catalyst.

Embodiment 12

The composite catalyst catalyzes a selective hydrogenation of 6,10-dimethyl-5-undecen-2-one (III) by following process.

Approximately 50 mg composite catalyst obtained in embodiment 1 was added to a 50 mL autoclave. Approximately 15 mmol 6,10-dimethyl-5-undecen-2-one (III) and about 5 mL ethanol were added. The reaction was taken under a hydrogen pressure of about 2 MPa, a reaction temperature of 30 degrees centigrade and reaction time of about 4 hours. A conversion of 6,10-dimethyl-5-undecen-2-one (III) was about 100%, and a selectivity of 6,10-dimethyl-undecyl-2-one (IV) was about 99%.

Embodiment 13

The composite catalyst catalyzes a selective hydrogenation of 6,10-dimethyl-5,9-undecenediene-2-one (V) by following process.

Approximately 50 mg composite catalyst obtained in embodiment 1 was added to a 50 mL autoclave. About 10 mmol 6,10-dimethyl-5,9-undecenediene-2-one (V) and about 5 mL ethanol were added. The reaction was taken under a hydrogen pressure of 2 MPa, a reaction temperature of 30 degrees centigrade and reaction time of 4 hours. A conversion of 6,10-dimethyl-5,9-undecenediene-2-one (V) was 100%, and a selectivity of 6,10-dimethyl-undecyl-2-one (IV) was 99%.

Embodiment 14

The composite catalyst catalyzes a selective hydrogenation of 6,10,14-trimethyl-5-pentadecen-2-one (VI) by following process.

Approximately 50 mg Composite catalyst obtained in Embodiment 1 was added to a 50 mL autoclave. Approximately 15 mmol 6,10,14-trimethyl-5-pentadecen-2-one (VI) and about 5 mL ethanol were added. The reaction was taken under a hydrogen pressure of about 2 MPa, a reaction temperature of about 30 degrees centigrade and reaction time of about 4 hours. A conversion of 6,10,14-trimethyl-5-pentadecen-2-one (VI) was about 100%, and a selectivity of 6,10,14-trimethyl-pentadecan-2-one (VII) was about 99%.

Embodiment 15

The composite catalyst catalyzes a selective hydrogenation of 6,10,14-trimethyl-5,9-pentadecandien-2-one (VIII) by following process.

Approximately 50 mg Composite catalyst obtained in embodiment 1 was added to a 50 mL autoclave. Approximately 10 mmol 6,10,14-trimethyl-5,9-pentadecandien-2-one (VIII) and about 5 mL ethanol were added. The reaction was taken under a hydrogen pressure of about 2 MPa, a reaction temperature of about 30 degrees centigrade and reaction time of about 4 hours. A conversion of 6,10,14-trimethyl-5,9-pentadecandien-2-one (VIII) was about 100%, and a selectivity of 6,10,14-trimethyl-pentadecan-2-one (VII) was about 99%.

Embodiment 16

The composite catalyst catalyzes a selective hydrogenation of 6,10,14-trimethyl-5,9,13-pentadecatrien-2-one (IX) by following process.

Approximately 50 mg Composite catalyst obtained in Embodiment 1 was added to a 50 mL autoclave. Approximately 5 mmol 6,10,14-trimethyl-5,9,13-pentadecatrien-2-one (IX) and about 5 mL ethanol were added. The reaction was taken under a hydrogen pressure of about 2 MPa, a reaction temperature of about 30 degrees centigrade and reaction time of about 3 hours. A conversion of 6,10,14-trimethyl-5,9,13-pentadecatrien-2-one (IX) was about 100%, and a selectivity of 6,10,14-trimethyl-pentadecan-2-one (VII) was about 98%.

Embodiment 17

The composite catalyst catalyzes a selective hydrogenation of 6-methyl-5-hepten-2-one (I) by following process.

Approximately 50 mg composite catalyst obtained in embodiment 6 was added to a 50 mL autoclave. Approximately 4 mmol 6-methyl-5-hepten-2-one (I) and about 5 mL ethanol were added. The reaction was taken under a hydrogen pressure of about 2 MPa, a reaction temperature of about 40 degrees centigrade and reaction time of about 4 hours. A conversion of 6-methyl-5-hepten-2-one (I) was about 100%, and a selectivity of 6-methyl-2-heptanone (II) was about 98%.

Embodiment 18

The composite catalyst catalyzes a selective hydrogenation of 6-methyl-5-hepten-2-one (I) by following process.

Approximately 50 mg composite catalyst obtained in embodiment 7 was added to a 50 mL autoclave. Approximately 2 mmol 6-methyl-5-hepten-2-one (I) and about 5 mL ethanol were added. The reaction was taken under a hydrogen pressure of about 2 MPa, a reaction temperature of about 40 degrees centigrade and reaction time of about 5 hours. A conversion of 6-methyl-5-hepten-2-one (I) was about 100%, and a selectivity of 6-methyl-2-heptanone (II) was about 97%.

Embodiment 19

The composite catalyst catalyzes a selective hydrogenation of 6-methyl-5-hepten-2-one (I) by following process.

Approximately 50 mg composite catalyst obtained in embodiment 8 was added to a 50 mL autoclave. Approximately 15 mmol 6-methyl-5-hepten-2-one (I) and about 5 mL ethanol were added. The reaction was taken under a hydrogen pressure of about 2 MPa, a reaction temperature of about 30 degrees centigrade and reaction time of about 4 hours. A conversion of 6-methyl-5-hepten-2-one (I) was about 100%, and a selectivity of 6-methyl-2-heptanone (II) was about 99%.

Embodiment 20

The composite catalyst catalyzes a selective hydrogenation of 6-methyl-5-hepten-2-one (I) by following process.

Approximately 50 mg composite catalyst obtained in embodiment 9 was added to a 50 mL autoclave. Approximately 15 mmol 6-methyl-5-hepten-2-one (I) and about 5 mL ethanol were added. The reaction was taken under a hydrogen pressure of about 2 MPa, a reaction temperature of about 30 degrees centigrade and reaction time of about 4 hours. A conversion of 6-methyl-5-hepten-2-one (I) was about 100%, and a selectivity of 6-methyl-2-heptanone (II) was about 99%.

Embodiment 21

The composite catalyst catalyzes a selective hydrogenation of 6-methyl-5-hepten-2-one (I) by following process.

Approximately 50 mg composite catalyst obtained in embodiment 10 was added to a 50 mL autoclave. Approximately 2 mmol 6-methyl-5-hepten-2-one (I) and about 5 mL ethanol were added. The reaction was taken under a hydrogen pressure of about 2 MPa, a reaction temperature of about 50 degrees centigrade and reaction time of about 6 hours. A conversion of 6-methyl-5-hepten-2-one (I) was about 100%, and a selectivity of 6-methyl-2-heptanone (II) was about 97%.

Embodiment 22

The composite catalyst catalyzes a selective hydrogenation of the biotin precursor (X) by following process.

Approximately 200 mg composite catalyst obtained in embodiment 1 was added to a 50 mL autoclave. Approximately 2 mmol biotin precursor (X) and about 5 mL ethanol were added. The reaction was taken under a hydrogen pressure of about 2 MPa, a reaction temperature of about 40 degrees centigrade and reaction time of about 3 hours. A conversion of biotin precursor (X) was about 100%, and a selectivity of biotin (XI) was about 99%.

Embodiment 23

The composite catalyst catalyzes a selective hydrogenation of the biotin precursor (X) by following process.

Approximately 200 mg composite catalyst obtained in embodiment 6 was added to a 50 mL autoclave. Approximately 2 mmol biotin precursor (X) and about 5 mL ethanol were added. The reaction was taken under a hydrogen pressure of about 2 MPa, a reaction temperature of about 50 degrees centigrade and reaction time of about 3 hours. A conversion of biotin precursor (X) was about 100%, and a selectivity of biotin (XI) was about 99%.

Embodiment 24

The composite catalyst catalyzes an application performance of the selective hydrogenation of 6-methyl-5-hepten-2-one (I) by following process.

Approximately 50 mg composite catalyst obtained in embodiment 1 was added to a 50 mL autoclave. Approximately 15 mmol 6-methyl-5-hepten-2-one (I) and about 5 mL ethanol were added. The reaction was taken under a hydrogen pressure of about 2 MPa, a reaction temperature of about 30 degrees centigrade and reaction time of about 4 hours. After the reaction, the composite catalyst was taken out by centrifugation, washed three times with ethanol, and dried under vacuum at about 40 degrees centigrade. The composite catalyst was continued to catalyze the selective hydrogenation of 2-methyl-3-butyn-2-ol (I). The results of the application were shown in Table 1. The result was the performance of the composite catalyst was stable, and the activity and selectivity of the composite catalyst was maintained after about 60 times of application.

TABLE 1

| Times | Conversion of one of 6-methyl-5-hepten-2-one (I) (%) | Selectivity of 6-methyl-2-heptanone (II) (%) | Hydrogenation selectivity (%) | Raw material selectivity (%) |
| --- | --- | --- | --- | --- |
| 1 | 100 | 99 | <1 | <1 |
| 3 | 100 | 99 | <1 | <1 |
| 6 | 100 | 99 | <1 | <1 |
| 9 | 100 | 99 | <1 | <1 |
| 12 | 100 | 99 | <1 | <1 |
| 15 | 100 | 99 | <1 | <1 |
| 20 | 100 | 99 | <1 | <1 |
| 25 | 100 | 99 | <1 | <1 |
| 30 | 100 | 99 | <1 | <1 |
| 35 | 100 | 99 | <1 | <1 |
| 40 | 100 | 99 | <1 | <1 |
| 45 | 100 | 99 | <1 | <1 |
| 50 | 100 | 99 | <1 | <1 |
| 55 | 100 | 99 | <1 | <1 |
| 60 | 99 | 99 | <1 | <1 |

Embodiment 25

The composite catalyst catalyzes an application performance of the selective hydrogenation of biotin precursor (X) by following process.

Approximately 200 mg composite catalyst obtained in embodiment 1 was added to a 50 mL autoclave. Approximately 2 mmol biotin precursor (X) and about 5 mL ethanol were added. The reaction was taken under a hydrogen pressure of about 2 MPa, a reaction temperature of about 40 degrees centigrade and reaction time of about 3 hours. After the reaction, the composite catalyst was taken out by centrifugation, washed three times with ethanol, and dried under vacuum at about 40 degrees centigrade. The composite catalyst was continued to catalyze the selective hydrogenation of biotin precursor (X). The results of the application were shown in Table 2. The result was the performance of the composite catalyst was stable, and the activity and selectivity of the composite catalyst was maintained after about 35 times of application.

TABLE 2

| Times | Conversion of one of biotin precursor (X) (%) | Selectivity of biotin (XI) (%) | Esterification product electivity (%) |
|---|---|---|---|
| 1 | 100 | 99 | <1 |
| 3 | 100 | 99 | <1 |
| 6 | 100 | 99 | <1 |
| 9 | 100 | 99 | <1 |
| 12 | 100 | 99 | <1 |
| 15 | 100 | 99 | <1 |
| 20 | 100 | 99 | <1 |
| 25 | 100 | 99 | <1 |
| 30 | 99 | 99 | <1 |
| 35 | 98 | 99 | <1 |

The technical features of the above-described embodiments may be combined in any combination. For the sake of brevity of description, all possible combinations of the technical features in the above embodiments are not described. However, as long as there is no contradiction between the combinations of these technical features, all should be considered as within the scope of this disclosure.

The above-described embodiments are merely illustrative of several embodiments of the present disclosure, and the description thereof is relatively specific and detailed, but is not to be construed as limiting the scope of the disclosure. It should be noted that a number of variations and modifications may be made by those skilled in the art without departing from the spirit and scope of the disclosure. Therefore, the scope of the disclosure should be determined by the appended claims.

We claim:

1. A method for manufacturing a composite catalyst comprising:
    dissolving a metal source in a solvent to obtain a premix;
    sequentially adding a nitrogen-containing biomass and a pore-forming agent to the premix, such that the metal source reacts with the pore-forming agent to obtain a mixture containing a metal precipitate, wherein the pore-forming agent is at least one of ammonium bicarbonate, ammonium carbonate, ammonium oxalate, ammonium hydrogen oxalate, oxalic acid, or a combination thereof, and a molar ratio of the metal source to the pore-forming agent is in a range of 1:1 to 1:20;
    treating the mixture by a first calcination at 500 degrees centigrade to 1200 degrees centigrade under an inert atmosphere to obtain a nitrogen-doped porous carbon composite material having a plurality of passages, wherein the nitrogen-doped porous carbon composite material comprises a nitrogen-doped porous carbon material and a plurality of metal oxide particles, the plurality of metal oxide particles are uniformly distributed in the nitrogen-doped porous carbon material, and a part of the plurality of metal oxide particles are exposed through the plurality of passages; and
    forming noble metal particles in the plurality of passages and combining noble metal atoms with oxide atoms of the exposed part of the plurality of metal oxide particles.

2. The method for manufacturing the composite catalyst of claim 1, wherein the forming the noble metal particles in the plurality of passages comprises:
    immersing the nitrogen-doped porous carbon composite material in a noble metal precursor solution; and
    treating the nitrogen-doped porous carbon composite material by a second calcination and a hydrogen reduction to obtain noble metal particles in the plurality of passages.

3. The method for manufacturing the composite catalyst of claim 2, wherein a noble metal precursor in the noble metal precursor solution is at least one of $PdCl_2$, $H_2PdCl_4$, $Pd(NO_3)_2$, $Pd(NH_3)_4(NO_3)_2$, $H_2PtCl_6 \cdot 6H_2O$, $[Pt(NH_3)_4](NO_3)_2$, $Na_2PtCl_4 \cdot xH_2O$, $H_8C_{14}N_2Pt$, $PtCl_4$, $Pt(C_5H_7O_2)_2$, $C_{10}H_{14}O_4Pt$, $(NH_4)_2RuCl_6$, $RuCl_3$, $C_{15}H_{21}O_6Ru$, $H_{12}Cl_6N_3Rh$, $RhN_3O_9$, $RhCl_3 \cdot 3H_2O$, $IrCl_3$, $Na_2IrCl_6 \cdot 6H_2O$, $H_2IrCl_6 \cdot xH_2O$, $[CH_3COCH=C(O-)CH_3]_3Ir$, $NaAuCl_4 \cdot 2H_2O$, $HAuCl_4 \cdot XH_2O$, $(NH_4)AuCl_4$, or a combination thereof.

4. The method for manufacturing the composite catalyst of claim 2, wherein in the second calcination, a calcination temperature is in a range of 200 degrees centigrade to 500 degrees centigrade, a heating rate is in a range of 1 degree centigrade per minute to 20 degrees centigrade per minute, the time is in a range of 1 minute to 240 minutes; in the hydrogen reduction, a reduction temperature is in a range of 150 degrees centigrade to 500 degrees centigrade, a heating rate is in a range of 1 degree centigrade per minute to 20 degrees centigrade per minute, the time is in a range of 1 minute to 360 minutes, and a flow rate of hydrogen gas is in a range of 20 milliliters per minute to 200 milliliters per minute.

5. The method for manufacturing the composite catalyst of claim 1, wherein the forming the noble metal particles in the plurality of passages comprises:
    immersing the nitrogen-doped porous carbon composite material in a noble metal precursor solution; and
    adding a reductant which reacts with a noble metal precursor of the noble metal precursor solution to obtain noble metal particles in the plurality of passages.

6. The method for manufacturing the composite catalyst of claim 5, wherein the noble metal precursor of the noble metal precursor solution is at least one of $PdCl_2$, $H_2PdCl_4$, $Pd(NO_3)_2$, $Pd(NH_3)_4(NO_3)_2$, $H_2PtCl_6 \cdot 6H_2O$, $[Pt(NH_3)_4](NO_3)_2$, $Na_2PtCl_4 \cdot xH_2O$, $H_8C_{14}N_2Pt$, $PtCl_4$, $Pt(C_5H_7O_2)_2$, $C_{10}H_{14}O_4Pt$, $(NH_4)_2RuCl_6$, $RuCl_3$, $C_{15}H_{21}O_6Ru$, $H_{12}Cl_6N_3Rh$, $RhN_3O_9$, $RhCl_3 \cdot 3H_2O$, $IrCl_3$, $Na_2IrCl_6 \cdot 6H_2O$, $H_2IrCl_6 \cdot xH_2O$, $[CH_3COCH=C(O-)CH_3]_3Ir$, $NaAuCl_4 \cdot 2H_2O$, $HAuCl_4 \cdot XH_2O$, $(NH_4)AuCl_4$, or a combination thereof.

7. The method for manufacturing the composite catalyst of claim 5, wherein the reductant is at least one of $NaBH_4$, $HCOOH$, and hydrazine hydrate, or a combination thereof, and a molar ratio of the reductant to the noble metal precursor of the noble metal precursor solution is in a range of 1:1 to 1000:1.

8. The method for manufacturing the composite catalyst of claim 1, wherein the metal source is at least one of cerium nitrate, zirconium nitrate, aluminum nitrate, or a combination thereof, the solvent is water, and the nitrogen-containing biomass is at least one of bamboo, chitin, carboxymethyl chitin, chitosan, carboxymethyl chitosan, glucosamine hydrochloride, or a combination thereof.

9. The method for manufacturing the composite catalyst of claim 1, wherein a mass ratio of the metal source to the nitrogen-containing biomass is in a range of 0.05:1 to 2:1.

10. The method for manufacturing the composite catalyst of claim 1, wherein a calcination time during the first calcination is in a range of 0.1 hour to 5 hours.

11. A composite catalyst manufactured by the method of claim 1 comprising a carrier and noble metal particles supported by the carrier, wherein the carrier is a nitrogen-doped porous carbon composite material having a plurality of passages, the nitrogen-doped porous carbon composite material comprises a nitrogen-doped porous carbon material and a plurality of metal oxide particles, the plurality of metal oxide particles are uniformly distributed in the nitrogen-doped porous carbon material, the plurality of metal oxide particles are partially exposed through the plurality of passages, noble metal atoms of the noble metal particles are tightly combined with oxide atoms of the exposed metal oxide particles to achieve recombination, and the noble metal particles are at least one of Pd metal particles, Pt metal particles, Ru metal particles, Rh metal particles, Ir metal particles, Au metal particles, or a combination thereof.

12. The composite catalyst of claim 11, wherein the noble metal particles have a dispersity of 75% to 95% in the nitrogen-doped porous carbon composite material.

13. The composite catalyst of claim 11, wherein a weight percentage of the noble metal particles in the composite catalyst is in a range of 0.1% to 10%, a weight percentage of the metal oxide particles in the composite catalyst is in a range of 2% to 30%, a weight percentage of the nitrogen-doped porous carbon composite material in the composite catalyst is in a range of 60% to 97.9%, and a weight percentage of nitrogen element in the nitrogen-doped porous carbon composite material is in a range of 0.5% to 15%.

* * * * *